US008828435B2

(12) United States Patent
Hewitt et al.

(10) Patent No.: US 8,828,435 B2
(45) Date of Patent: Sep. 9, 2014

(54) BUCCAL DELIVERY SYSTEM

(75) Inventors: Ernest Alan Hewitt, Windsor Downs (AU); Richard James Stenlake, Double Day (AU)

(73) Assignee: Lingual Consegna Pty Ltd (AU)

( * ) Notice: Subject to any disclaimer, the term of this patent is extended or adjusted under 35 U.S.C. 154(b) by 85 days.

(21) Appl. No.: 13/021,578

(22) Filed: Feb. 4, 2011

(65) Prior Publication Data

US 2011/0123619 A1 May 26, 2011

Related U.S. Application Data

(63) Continuation of application No. 11/910,902, filed as application No. PCT/AU2006/000472 on Apr. 7, 2006, now abandoned.

(51) Int. Cl.
*A61K 9/14* (2006.01)
*A61K 9/20* (2006.01)
*A61K 9/00* (2006.01)

(52) U.S. Cl.
CPC ............. *A61K 9/0056* (2013.01); *A61K 9/2031* (2013.01); *A61K 9/2095* (2013.01)
USPC .......................................... 424/484; 514/108

(58) Field of Classification Search
CPC .. A61K 9/2031; A61K 9/2095; A61K 9/0056
USPC ........................................................ 424/484
See application file for complete search history.

(56) References Cited

U.S. PATENT DOCUMENTS

| | | | |
|---|---|---|---|
| 4,146,634 A | 3/1979 | Brown et al. | |
| 4,764,378 A * | 8/1988 | Keith et al. | 424/435 |
| 5,244,668 A | 9/1993 | Snipes | |
| 5,324,746 A * | 6/1994 | McKee et al. | 514/530 |
| 5,891,465 A * | 4/1999 | Keller et al. | 424/450 |
| 5,945,117 A | 8/1999 | El-Rashidy et al. | |
| 6,117,446 A | 9/2000 | Place | |
| 6,180,682 B1 | 1/2001 | Place | |
| 6,193,992 B1 | 2/2001 | El-Rashidy et al. | |
| 6,319,510 B1 * | 11/2001 | Yates | 424/404 |
| 6,372,728 B1 * | 4/2002 | Ungell | 514/109 |
| 2002/0114833 A1 | 8/2002 | Abu-Izza et al. | |
| 2004/0019026 A1 * | 1/2004 | Schwartz | 514/177 |
| 2004/0028732 A1 | 2/2004 | Falkenhausen et al. | |
| 2004/0037878 A1 | 2/2004 | Szamosi et al. | |
| 2006/0141027 A1 | 6/2006 | Cioli | |

FOREIGN PATENT DOCUMENTS

| | | |
|---|---|---|
| EP | 215635 | 3/1987 |
| GB | 1248189 | 9/1971 |
| GB | 2394415 | 4/2004 |
| WO | WO9852541 | 11/1998 |
| WO | WO9904758 | 2/1999 |
| WO | WO0189485 | 11/2001 |
| WO | 2004075877 A1 | 9/2004 |

OTHER PUBLICATIONS

Velaz I., et al., "Effect of PEG 4000 on the Dissolution Rate of Naproxen", European Journal of Drug Metabolism & Pharmacokinetics, vol. 23, No. 2, pp. 103-108 (Apr.-Jun. 1998).
Runkel, R., et al., "Naproxen Oral Absorption Characteristics", Chem. Pharm. Bull. vol. 70, No. 7, pp. 1457-1466 (197p).
Ranucci E., et al., "Pharmacokinetic Results on Naproxen Prodrugs Based on Poly(ethyleneglycol)s", J Biomater Sci Polymer Edn, vol. 6, No. 2, pp. 141-147 (1994).
Ali, J., et al., "Formulation and Characterisation of a Buccoadhesive Erodible Tablet for the Treatment of Oral lesions", Dept. of Pharmaceutics, Faculty of Pharmacy, Hamdard University, New Delhi, India, pp. 329-334 (1998).
Extended European Search Report for corresponding International Application PCT/AU06/000472, Dec. 16, 2011.

* cited by examiner

*Primary Examiner* — Adam C Milligan
(74) *Attorney, Agent, or Firm* — Maryellen Feehery Hank; Reed Smith LLP (57) ABSTRACT

A buccal delivery system capable of being blended in a normal dry powder process and compressed using a standard tabletting machine, said buccal delivery system comprising a matrix of: (a) an effective amount of one or more active ingredients; (b) an amount of one or more polyethylene glycols or derivatives thereof having a molecular weight between 1000 to 8000 sufficient to provide the required hardness and time for dissolution of the matrix; (c) 0.05-2% by weight of the total matrix of one or more suspending agents; (d) 0.05-2% by weight of the total matrix of one or more flowing agents; and (e) 0.05-2% by weight of the total matrix of one or more sweeteners.

8 Claims, 4 Drawing Sheets

Figure 6: TABLE 5

OESTRADIOL (pmol/L)

| Time | Pre-Dose | | 1.0 hour | | 4.0 hours | | 8.0 hours | | 12.0 hours | | 16.0 hours | | 24.0 hours | |
|---|---|---|---|---|---|---|---|---|---|---|---|---|---|---|
| | Mean | Standard Deviation | Mean | Standard Deviation | Mean | Standard Deviation | Mean | Standard Deviation | Mean | Standard Deviation | Mean | Standard Deviation | Mean | Standard Deviation |
| Blood | 72 | 114 | 1685 | 1072 | 229 | 61 | 100 | 59 | 60 | 28 | 53 | 39 | 30 | 18 |
| Saliva | 61 | 85 | 600 | 0 | 600 | 0 | 600 | 0 | 600 | 0 | 594 | 16 | 459 | 164 |

PROGESTERONE (pmol/L)

| Time | Pre-Dose | | 1.0 hour | | 4.0 hours | | 8.0 hours | | 12.0 hours | | 16.0 hours | | 24.0 hours | |
|---|---|---|---|---|---|---|---|---|---|---|---|---|---|---|
| | Mean | Standard Deviation | Mean | Standard Deviation | Mean | Standard Deviation | Mean | Standard Deviation | Mean | Standard Deviation | Mean | Standard Deviation | Mean | Standard Deviation |
| Blood | 1400 | 700 | 21400 | 6900 | 12200 | 9100 | 4500 | 2200 | 2900 | 1100 | 2600 | 900 | 2700 | 600 |
| Saliva | 378 | 430 | 22260 | 0 | 22260 | 0 | 19791 | 6049 | 9535 | 8176 | 12257 | 11061 | 5272 | 5045 |

TESTOSTERONE (pmol/L)

| Time | Pre-Dose | | 1.0 hour | | 4.0 hours | | 8.0 hours | | 12.0 hours | | 16.0 hours | | 24.0 hours | |
|---|---|---|---|---|---|---|---|---|---|---|---|---|---|---|
| | Mean | Standard Deviation | Mean | Standard Deviation | Mean | Standard Deviation | Mean | Standard Deviation | Mean | Standard Deviation | Mean | Standard Deviation | Mean | Standard Deviation |
| Blood | 400 | 100 | 23500 | 5400 | 2900 | 1200 | 900 | 500 | 500 | 200 | 500 | 300 | 600 | 200 |
| Saliva | 74 | 39 | 2500 | 0 | 2500 | 0 | 1527 | 1046 | 551 | 417 | 569 | 438 | 356 | 258 |

DHEAS (nmol/L)

| Time | Pre-Dose | | 1.0 hour | | 4.0 hours | | 8.0 hours | | 12.0 hours | | 16.0 hours | | 24.0 hours | |
|---|---|---|---|---|---|---|---|---|---|---|---|---|---|---|
| | Mean | Standard Deviation | Mean | Standard Deviation | Mean | Standard Deviation | Mean | Standard Deviation | Mean | Standard Deviation | Mean | Standard Deviation | Mean | Standard Deviation |
| Blood | 1500 | 600 | 2200 | 600 | 2600 | 700 | 2400 | 500 | 2000 | 600 | 1700 | 300 | 2000 | 700 |
| Saliva | 7 | 7 | 44 | 27 | 32 | 12 | 31 | 18 | 19 | 8 | 31 | 14 | 21 | 12 |

BUCCAL DELIVERY SYSTEM

RELATED APPLICATION

This instant application is a continuation of application Ser. No. 11/910,902 filed on Oct. 5, 2007, with a 371(c) filing date of Feb. 5, 2008, which is a U.S. National Phase Application of International Application Serial No. PCT/AU2006/000472, filed Apr. 7, 2006, which claims priority to Australian Application Serial No. AU 2005901758 filed Apr. 8, 2005.

FIELD OF THE INVENTION

The invention relates to a buccal delivery system which provides improved delivery of therapeutic agents. In particular, the present invention relates to buccal dosage formulations. The present invention further provides easier and more economic methods of manufacturing a dosage formulation capable of delivering one or more active ingredients via buccal membranes.

BACKGROUND OF THE INVENTION

In this specification where a document, act or item of knowledge is referred to or discussed, this reference or discussion is not an admission that the document, act or item of knowledge or any combination thereof was at the priority date, publicly available, known to the public, part of common general knowledge; or known to be relevant to an attempt to solve any problem with which this specification is concerned.

The ability to effectively deliver therapeutic agents to animals and, in particular, humans is frequently dependent on compliance of the recipient. Compliance is also often connected or associated with the formulation used to deliver the agent. The formulations provided are also dependent on the ease of manufacture.

In addition, the formulation itself is often critical to the efficacy of the drug to be delivered. This is particularly the case for the delivery of pain relief agents such as paracetamol. One of the rate limiting steps in paracetamol delivery to the blood stream is the rate of gastric emptying. Various formulations which provide paracetamol at an alkaline pH have been proposed.

There is a continual need to develop more improved drug delivery formulations which efficaciously deliver therapeutic agents quickly yet without inducing unwanted side effects.

A major objective in drug delivery is to obtain a specific biological effect at a targeted site of action with minimal side effects. It is taught that bioactivity of a pharmaceutical will be sub-optimal if it does not possess the correct physiochemical properties to allow release of the biologically active form. For this reason improved drug delivery strategies focus on modifying physiochemical properties of active drugs including solubility, dissolution and dispersion.

Troches

Back in the 1800's, medical lozenges were extensively used to treat mouth and throat infections. These were small, square shape, mildly medicated solid masses intended to dissolve in the mouth. The finished troches are dispensed in plastic calibrated moulds that contain an accurate and precise dosage unit. In England they were called a lozenge, in the USA a troche, in France a tablette, and in Germany a pastillen. Troches slowly melt in the mouth and the active ingredients are absorbed mostly by the soft lining of the inner cheek. Here, blood vessels carry the hormones off to the rest of the body, similar to an injection with a needle.

Troches first appeared in the Edinburgh Pharmacopoeia in 1841 and then in 1864 in the British Pharmacopoeia. In the 1800s, troche making was an art way and required a lot of practical experience. The apparatus required to make troches was a smooth marble slab to mix them, a rolling pin, troche cutters, a palette knife, a badger brush with long soft hairs, linen cloth, and troche trays.

Today the computer has replaced the marble slabs, the wooden trays and brushes, etc. with complex electronic mixers, poly-glycol flavoured bases, accurate electronic scales (capable of measuring milligram doses) and miniature electric hot plates that make the finished troche an accurate and precise dosage form. The finished troches are dispensed in plastic calibrated moulds. The troches are available in a wide variety of flavours to assist compliance by even the fussiest patient.

The troches provide a means to deliver custom made medication in small doses directly into the blood stream. Today many drugs, both natural and synthetic, can be used in troche form to gain rapid onset of action and bypass the usual absorption into the blood stream, thus bypassing the liver. This reduces the load upon the liver and is especially good for liver toxic drugs.

Troches are currently used in hormone replacement therapy mainly because of the ease in which ingredients in each prescription can be altered and the buccal absorption does not involve gastric metabolism. Troches can also be mixed so that each individual troche contains a combination of various natural hormones in small doses. For example, a troche can be made containing a mixture of any of the bio-identical natural hormones, eg: estrogen, progesterone, testosterone and DHEA in any possible dosage. This combination is used to treat the symptoms of menopause. For male andropause, a combination of testosterone and DHEA is most commonly used. Troches containing natural progesterone alone are helpful for premenstrual syndrome and can be taken during the latter half of the menstrual cycle to alleviate depression, migraine, nausea and basically all those PMT symptoms that occur in the premenstrum.

They are also used for anaesthetics, antibiotics, analgesics, antimicrobials, antitussives, demulcents and other combinations of medicines.

Troches are being marketed as a method of administering agents that bypass the stomach and first pass metabolism of the liver as they are supposedly absorbed directly into buccal circulation. Claims are made that this places less stress on the liver and therefore is better for the patient. In reality, more than 50% (up to 70%) of the troche dose is actually swallowed by the normal salivation process which will encounter the stomach acids and first pass metabolism while the remainder is absorbed by the buccal mucosa (*Int J Pharm Comp.*, 4, 414-420, 2000). With only 30 to 50% of the dose being absorbed through the mucosal lining in the mouth there appears to be only a minimal reduction in the livers first pass metabolism when compared to capsules. The hormones that are eventually absorbed, whether it is by the buccal mucosa or the gastrointestinal tract, will eventually encounter the liver anyway at some stage through normal circulation so there is no real significant liver sparing effect. Clinical experience shows that the doses required for troches are within the same range as those required for capsules so the overall "total load" on the body is approximately the same so again no real liver sparing benefit is obtained. Creams on the other hand require lower doses compared to troches and capsules and actually do bypass the stomach and first pass metabolism of the liver so are therefore the only way that actually reduces the overall load on the liver.

Hormones that possess poor oral bioavailability such as progesterone and testosterone (10 to 15% bioavailability) could potentially be good candidates for buccal administration. If successful the dosages for buccal administration should approach those of normal physiological doses e.g. progesterone 20 to 40 mg daily as found with creams. Clinical experience shows that the doses of progesterone needed in troches is usually between 200 to 400 mg daily which indicates a great deal of the dose is not being absorbed by the buccal mucosa thus supporting the evidence that a majority of the dose is being swallowed. Perhaps a buccal patch would provide better absorption characteristics than troches but are currently unavailable. In addition, there is no real benefit using buccal administration over oral administration for those hormones such as the estrogens and DHEA which already possess good oral bioavailability (over 90%).

Troches also exhibit poor pharmacokinetic parameters. This means that there are great fluctuations in hormone serum levels after taking a troche dose. Soon after taking a troche serum hormone levels rise rapidly, sometimes to very high levels, and then rapidly fall to low levels within 4 to 5 hours. They therefore require at least twice daily administration or for optimal results three to four times a day to maintain adequate levels longer however compliance becomes a major problem with this type of dosing schedule. This wide fluctuation in hormone levels is not the ideal situation. Creams and slow release capsules release hormones into the blood stream more gradually achieving steadier serum levels for a longer period of time thus generally requiring only once a day dosing.

Troches are made from two different types of bases both of which have several drawbacks:
- polyethylene glycol (PEG)—PEG bases are well known to cause allergic and sensitivity reactions and can cause the buccal mucosa to become inflamed. In addition PEG's can contain small amounts of dioxin, an industrial solvent shown to cause cancer; and
- gelatin—is a hydrophilic (water loving) base which causes hydrophobic (fat loving) particles such as bioidentical hormones to aggregate together. This aggregation of particles further reduces mucosal absorption thus increasing the amount swallowed and also does not allow for an even dispersion of the hormones throughout the slurry causing greater dose variation between each troche made.

In conclusion troches are currently being widely used to administer bioidentical hormones to women however they possess many drawbacks and are not considered the optimal choice. Transdermal creams are considered the first choice by many as they require lower doses compared to troches and capsules and they are the only route of administration that truly bypasses the stomach and first pass metabolism. They provide better release parameters providing steady serum levels without wild fluctuations seen with troches. They only require once daily dosing so are more convenient, dosage adjustments are very easy to make and finally they are significantly cheaper with a standard formula costing about $30/month. If creams are deemed unsuitable in certain cases then the second choice should be slow release capsules. These capsules provide better release properties than troches, only require once a day dosing, and are fast to administer and no bitter taste. Troches are thought to be suitable for patients where creams are unsuitable and malabsorption syndrome occurs thus making oral administration unsuitable.

There is thus a need for improved formulations for sublingual or buccal delivery of agents to patients.

Bisphosphonates

One group of drugs which is particularly beneficial in a range of conditions are the bisphosphonates. Osteoporosis is one condition for which the bisphosphonate drugs, alendronate and risedronate, are frequently prescribed.

Osteoporosis and selected bone-resorptive conditions represent a significant medical disorder affecting millions of sufferers worldwide. Examples of other bone-resorptive conditions include other diseases or physiological states where there is an actual reduction or risk of reduction in bone mineral density and osteolysis from a normal reference range as a consequence of the disease or physiological state, such as menopause, hypogonadism, osteogenesis imperfecta, Paget's disease, myeloma bone disease, cancers metastatic to bone, primary hyperparathyroidism, fibrous dysplasia and hypercalcemia of malignancy.

For example, an estimated 44 million people in the United States over the age of 50 currently have either osteoporosis or low bone mass. This number could rise to over 61 million by 2020 (National Osteoporosis Foundation America's Bone Health: The State of Osteoporosis and Low Bone Mass, 2002).

Sufferers of osteoporosis face long-term drug therapy with anti-resorptive agents to prevent further bone loss. As indicated above, alendronate and risedronate are generally prescribed as anti-resorptive agents.

However, both agents are poorly absorbed (about 1% of the ingested dose), and this rate can be even lower if the drugs are not taken as directed. Non-compliance with current administration protocols is a common problem due to the gastrointestinal irritation of bisphosphonates which often leads to nausea and even vomiting in some subjects.

Bisphosphonates are also often prescribed in conjunction with hormone replacement therapy (HRT) to counter the effects of declining sex hormone production around the time of menopause. Sex hormone supplementation generally employs the gastrointestinal administration route, where significant amounts of hormone are degraded by the digestive environments encountered prior to absorption. As such, larger than required amounts of hormones must be used in the manufacture of oral hormone dosage forms to ensure a therapeutic dose reaches the circulation.

A number of HRT regimens specific for female menopausal symptoms have been devised, which have met with varying rates of clinical success. The majority of these treatments are based on the use of natural 17-β-oestradiol, conjugated equine oestrogen, or other conjugated oestrogens in combination with synthesised progestogens such as norethisterone, levonorgestrel and dydrogesterone. Although such therapeutic combinations are highly successful in controlling symptoms, again patient compliance is often a limiting factor in their overall clinical efficiency. Side-effects such as gastrointestinal irritation and bloating are unacceptable to many patients.

Poor patient compliance is a significant barrier to the completion of prescription regimens and the cause of sub-optimal clinical outcome. There is thus a need to develop drug delivery formulations which reduce the side-effects that impact on patient compliance.

SUMMARY OF THE INVENTION

The present invention provides a buccal delivery system which provides improved bioavailability of active agents. The buccal delivery system of the present invention is able to deliver up to and sometimes more than 85% of the active ingredient as it circumvents the action of the liver in 'first past metabolism'. In this specification, the term "buccal" is used in its broadest sense to refer to the mouth as a whole and includes sublingual.

Since the buccal delivery system of the present invention provides improved bioavailability, it is possible using the present invention to use less of the active ingredient in the manufacture of dosage forms.

In addition, the buccal delivery system of the present invention may reduce the severity of gastrointestinal side-effects of particular agents such as indigestion, pain, nausea, vomiting, constipation, cramps, diarrhoea and flatulence.

The present invention also provides a buccal delivery system which can be manufactured more easily and more economically as it can be made using a dry manufacturing process with all actives blended in a normal dry powder process and compressed using a standard tabletting machine. Such dry formulations can be manufactured in commercial numbers and provided in conventional blister packaging. The active ingredients and excipients are similar to those used in the prior art troche, however the excipients are modified so that there is no need to use the special wet formulating plant and equipment and manual processing required for the troches (soft gel products) of the prior art which are costly and time intensive.

According to a first aspect of the invention there is provided a buccal delivery system capable of being blended in a normal dry powder process and compressed using a standard tabletting machine, said buccal delivery system comprising a matrix of:
  (a) an effective amount of one or more active ingredients;
  (b) an amount of one or more polyethylene glycols or derivatives thereof having a molecular weight between 1000 to 8000 sufficient to provide the required hardness and time for dissolution of the matrix;
  (c) 0.05-2% by weight of the total matrix of one or more suspending agents;
  (d) 0.05-2% by weight of the total matrix of one or more flowing agents; and
  (e) 0.05-2% by weight of the total matrix of one or more sweeteners.

The effective amount of the active ingredient is typically an amount up to about 60% by weight of the total matrix.

The matrix may release the active ingredient from within seconds to hours of application depending on the desired release profile. Typically, the active ingredient is releasable from the matrix within at least two hours following application to one or more membranes in the buccal cavity, preferably within one hour of application and even more preferably within 40 minutes of application. Most preferably, dissolution occurs within 12 to 15 minutes. For acute treatments, preferably the matrix should be dissolved within 5 minutes of application.

The term "buccal delivery system" as used herein refers to a delivery system wherein an active ingredient is provided for absorption across one or more membranes in the mouth, including the buccal mucosa, buccal gingiva, mucous membrane of the tongue, sublingual membrane and the soft palate. The term encompasses all suitable dosage forms capable of manufacture using a normal dry powder process and compression using a standard tabletting machine.

Reference to an "active ingredient" includes a therapeutic or prophylactic agent, drug, pro-drug, drug complex, drug intermediate, diagnostic agent, enzyme, medicine, plant extract, herbal concoction, phytochemical, proteins, antibody, nanobody, antibody fragment, antibody directed enzyme pro-drug therapy (ADEPT), bioactive compound, nutraceutical or dietary supplement.

The term "matrix" as used herein refers to a solid or semi-solid monolithic material containing one or more dissolved or dispersed active ingredients closely associated with a surrounding, rate-controlling heterogenous material where the active ingredient(s) are released when the matrix is placed in direct contact with a moist diffusion membrane. The solid or semi solid monolithic material can include a range of materials known in the art of pharmaceutical drug delivery to emulsify, solubilize, complex or deliver any biologically active lipophilic or hydrophilic compound across a membrane.

The person skilled in the art will know which polyethylene glycol (PEG) is suitable to provide the desired pharmacokinetics for the delivery system. For example, the choice of PEG will be related to whether zero or first order release is desired. In a particularly preferred embodiment, the base is PEG 1450.

The polyethylene glycol can be used in the form of a PEG-fatty acid ester having surfactant properties. Examples of suitable PEG-fatty acid esters include PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, PEG-1450, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, a poloxamer, and mixtures thereof.

A person skilled in the art will understand that amount of the suspending agent is sufficient to improve the texture and consistency of the delivery system. Suitable examples of such suspending agents are those in the gum-yielding plant group such as tetragonolobus, *Acacia glaucophylla*, *Acacia abyssinica*, *Acacia nilotica*, *Acacia gummifera* and *Acacia arabica*. Other suitable suspending agents include silica gel and suspension polymers such as kollidon, cremaphor, kollicoat, solutol and ludipress.

The person skilled in the art will understand that the flowing agent (also known as lubricant) is present in an amount sufficient for the prevention of adhesion, especially during the manufacturing process. A suitable example of a flowing agent is magnesium stearate.

The buccal delivery system comprises a sufficient amount of a sweetener to improve the organoleptic properties of the dosage form. Examples of suitable sweeteners include sucrose, sucralose; zinc gluconate; ethyl maltitol; glycine; acesulfame-K; aspartame; saccharin; fructose; xylitol; honey; corn syrup, golden syrup, misri, spray dried licorice root; glycerrhizine; dextrose; sodium gluconate; stevia powder; glucono delta-lactone; ethyl vanillin; vanillin; normal and high-potency sweeteners or syrups or salts thereof. Preferably, a high-intensity sweetener selected from the group consisting of aspartame, sucralose, and acesulfame-K is used.

In another aspect, the present invention provides a method of manufacturing a dosage formulation capable of delivering one or more active ingredients across one or more membranes within the buccal cavity, said method comprising the steps of:
(a) preparing a matrix by blending
  (i) an effective amount of one or more active ingredients;
  (ii) an amount of one or more polyethylene glycols or derivatives thereof having a molecular weight between 1000 to 8000 sufficient to provide the required hardness and time for dissolution of the matrix;
  (iii) 0.05-2% by weight of the total matrix of one or more suspending agents;
  (iv) 0.05-2% by weight of the total matrix of one or more flowing agents; and
  (v) 0.05-2% by weight of the total matrix of one or more sweeteners.
(b) compressing the matrix into a suitable tablet format for administration to the one or more membranes in the buccal cavity;
wherein the ratio of active ingredients and excipients enables dissolution and absorption of the active ingredient within a desired time period.

Examples of suitable active ingredients include, but are not limited to, anti-infective agents (antibiotics), eye, ear, nose and throat preparations, anti-neoplastic agents including antibody, nanobody, antibody fragment(s), antibody directed enzyme pro-drug therapy (ADEPT), gastrointestinal drugs, respiratory agents, arthritic agents, blood formation and coagulation agents, diagnostic agents, photosensitisers (eg porphyrins and agents which stimulate natural porphyrin production), statins, naproxyn, indole-3-acetic acid, hormones and synthetic substitutes, cardiovascular drugs, skin and mucous membrane preparations, NSAIDs, analgesics, muscle spasm medications, anti-inflammatory agents, central nervous system drugs, dietary supplements, diabetic agents, and electrolyte and water balance agents, mixtures thereof and pro-drugs, drug complexes, drug intermediates, enzyme, vitamins and protein complexes thereof.

Other active ingredients include for example hormones of natural or synthetic origin selected from the hormone group comprising insulin, triamcinolone, testosterone, levonorgestrel, estradiol, phytoestrogen, estrone, dexamethasone, ethynodiol, prednisone, desogestrel, cyproterone, norethindrone, megestrol, hydrocortisone, danazol, cortisone acetate, aviane, nandrolone, fluoxymesterone, fludrocortisone, fluoxymesterone dexamethasone levora fludrocortisone lowogestrel methylprednisolone, necon, levonorgestrel, estropipate, levoxyl, methimazole, propylthiouracil desmopressin, prednisolone orgestrel norethindrone triamcinolone trivora zovia gestodene, alfacalcidol, 1,25-dihydroxyvitamin D3, clomiphene, finasteride and tibolone or any biologically relevant intermediate or combination thereof.

In one preferred embodiment, the active ingredient is a bisphosphonic acid or a bisphosphonate salt useful in the treatment of a bone resorptive condition. Reference to "a bisphosphonic acid" includes one or more acids as well as pharmaceutically acceptable salts and derivatives thereof. This term may be used to refer to a salt form such as "biphosphonate". Preferred bisphosphonic acids and their salts include the group comprising alendronate, etidronate, pamidronate, tiludronate and risedronate compounds. Even more preferably, the bisphosphonate is alendronate selected from the group comprising anhydrous alendronate or hydrated alendronate salts, such as sodium alendronate.

The buccal delivery system of the present invention may contain two or more active agents. The active ingredients may be released at the same time, ie simultaneously, or at differential rates. A preferred combination is one or more bisphosphonic acids (or salts thereof) with one or more hormones used in hormone replacement therapy, such as estradiol, progesterone, testosterone and/or dehydroepiandrosterone (DHEA).

The art of efficient drug delivery also requires that a drug be both soluble in the aqueous biological medium and in an appropriate form to permit transport of either individual drug molecules or very small aggregates of the drug molecules. The buccal delivery system may further comprise one or more other pharmaceutically acceptable carriers and/or excipients, such as but not limited to binding agents, flavouring agents, colouring agents, solubility enhancers, disintegrants, fillers, proteins, co-factors, emulsifiers, and solubilizing or complexing agents. In a preferred embodiment, these excipients will improve delivery of the active ingredient across a membrane. Suitable excipients will be known to those skilled in the art. One typical example of an emulsifier which may be suitable is tocopherol polyethylene glycol 1000 succinate (TPGS). Examples of complexing agents are compounds containing amine groups or other nitrogen functional groups such as amino acids, proteins, amine functional sterols and phospholipids containing amine functional groups. Suitable surfactants may be amphoteric, zwitterionic, or cationic. Preferred complexing agents of this type include water-soluble cationic polymers with a quaternary ammonium functional group on the polymer backbone and water-soluble, cationic guar (jaguar gums).

In a preferred embodiment, the buccal delivery system comprises a binding and gelling agent such as hydroxypropyl methocellulose.

In another embodiment, the buccal delivery system further comprises a colouring agent which may be a dye or a pigment. Suitable colouring agents are well known in the art and include curcumin, carotenoids, sunset yellow, tartrazine, indigo dyes, quino-phthalene dyes and triphenyl methane dyes.

In a preferred embodiment, the buccal delivery system further comprises a flavouring agent for improving organoleptic properties. Suitable flavouring agents are well known in the art and include almond oil; babassu oil; borage oil; blackcurrant seed oil; canola oil; castor oil; coconut oil; corn oil; cottonseed oil; evening primrose oil; grapeseed oil; groundnut oil; mustard seed oil; olive oil; palm oil; palm kernel oil; peanut oil; grapeseed oil; safflower oil; sesame oil; shark liver oil; soybean oil; sunflower oil; hydrogenated castor oil; hydrogenated coconut oil; hydrogenated palm oil; hydrogenated soybean oil; hydrogenated vegetable oil; hydrogenated cottonseed and castor oil; partially hydrogenated soybean oil; soy oil; glyceryl tricaproate; glyceryl tricaprylate; glyceryl tricaprate; glyceryl triundecanoate; glyceryl trilaurate; glyceryl trioleate; glyceryl trilinoleate; glyceryl trilinolenate; glyceryl tricaprylate/caprate; glyceryl tricaprylate/caprate/laurate; glyceryl tricaprylate/caprate/linoleate; glyceryl tricaprylate/caprate/stearate; saturated polyglycolized glycerides; linoleic glycerides; caprylic/capric glycerides; modified triglycerides; fractionated triglycerides; safrole, vanillin, citric acid, malic acid and phosphoric acid or salts and/or mixtures thereof.

In an alternative embodiment, the buccal dosage forms are useful as sustained release compositions. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period.

The present invention further contemplates methods of treatment and/or prophylaxis of medical conditions in mammals and, in particular, humans by the administration of a drug using a delivery system according to the invention.

DRAWINGS

Various embodiments/aspects of the invention will now be described with reference to the following drawings in which:

FIG. 6 is a tabular representation showing the results obtained for all of the hormones tested using a buccal delivery system according to the invention in Example 3.

EXAMPLES

Figure 1:
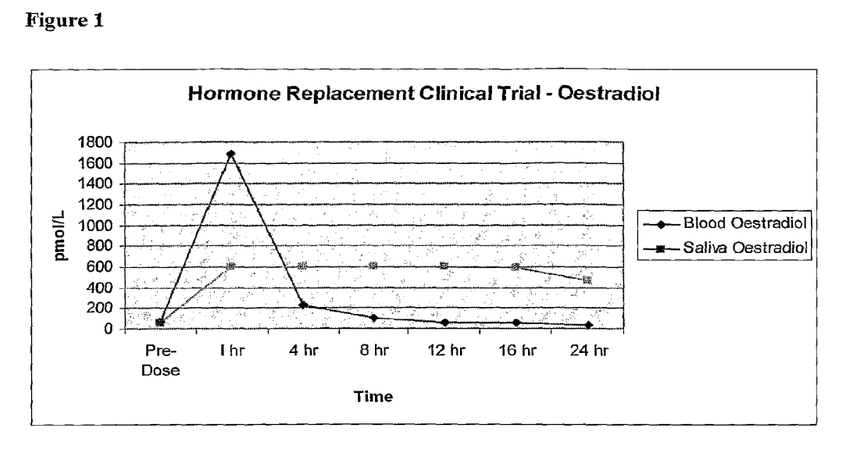
FIG. 1 is a diagrammatic representation showing the results obtained for oestradiol using a buccal delivery system according to the invention in Example 3.
Figure 2:
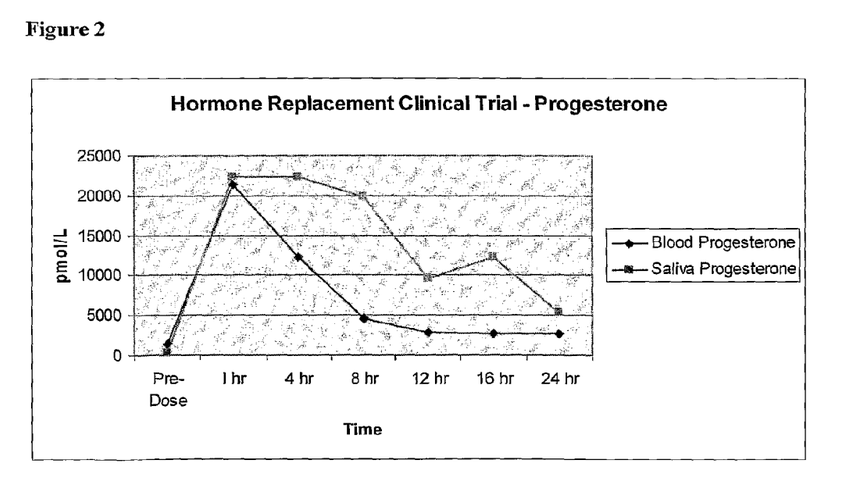
FIG. 2 is a diagrammatic representation showing the results obtained for progesterone using a buccal delivery system according to the invention in Example 3.
Figure 3:
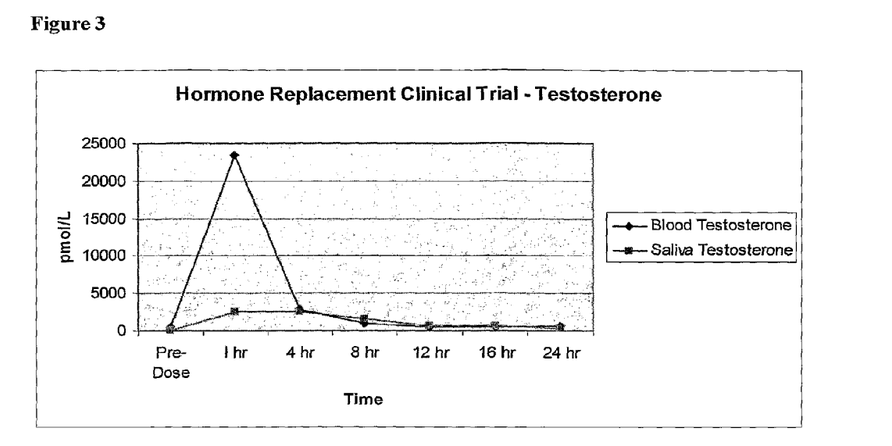
FIG. 3 is a diagrammatic representation showing the results obtained for testosterone using a buccal delivery system according to the invention in Example 3.
Figure 4:
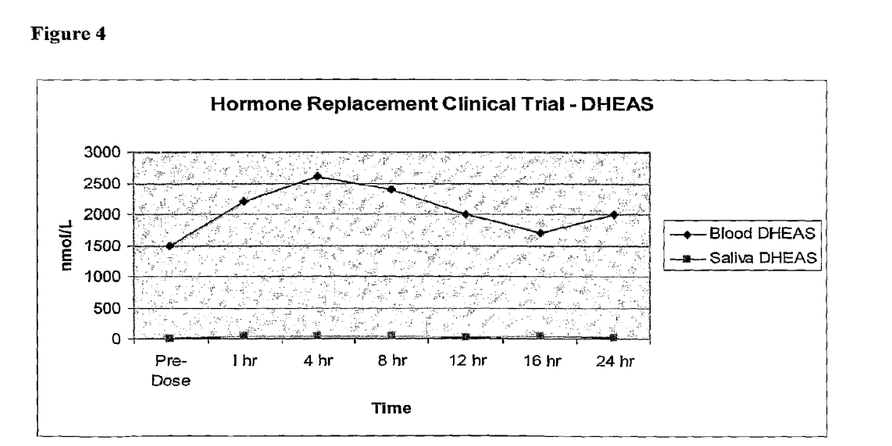
FIG. 4 is a diagrammatic representation showing the results obtained for dehydroepiandrosterone-sulphate using a buccal delivery system according to the invention in Example 3.
Figure 5:
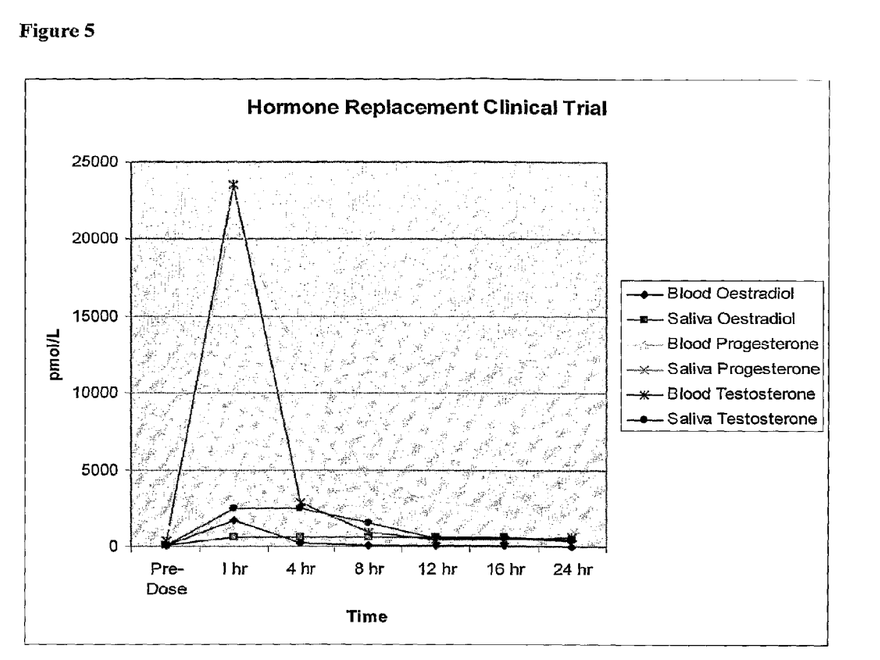
FIG. 5 is a diagrammatic representation showing the results obtained for all of the hormones tested using a buccal delivery system according to the invention in Example 3.

Various embodiments/aspects of the invention will now be described with reference to the following non-limiting examples.

Example 1

Comparative Example

This example shows the process for preparation of troches as per the prior art.

The ingredients used for 28 Troches is shown in Table 1.

TABLE 1

| Ingredients | |
| --- | --- |
| Drug | Amounts |
| *Stevia* powder | 130 mg |
| Methocel E4M | 1.45 g |
| Base A PEG 1450 | q.s to 30 g |
| Flavour | 60 uL-800 uL |

Preparation of Components

The required quantity of active ingredients is calculated (e.g. 200 mg progesterone for 30 lozenges requiring 6.0 g of progesterone).

Required components are weighed out and placed into clean labelled weigh trays (eg 0.01 g).

Preparation of PEG Base

In a large 4 liter beaker, the base required for the day is calculated (see Table 2) and placed on the hotplate to melt inside a water bath. The bath is set at 60° C.

Once Base A is melted, the other ingredients are added and stirred with a spatula.

TABLE 2

| | Approx 1 troches (29 mls) | Approx 25 troches (725 mls) | Approx 50 troches (1450 mls) | Approx 75 troches (2175 mls) | Approx 100 troches (2900 mls) |
| --- | --- | --- | --- | --- | --- |
| Base A | 28.10 g | 702.5 g | 1405 g | 2107.5 g | 2810.0 g |
| *Stevia* | 0.605 g | 15.125 g | 30.25 g | 45.375 g | 60.50 g |
| Acacia | 0.483 g | 12.075 g | 24.15 g | 36.225 g | 48.3 g |
| Methocel | 1.450 g | 36.25 g | 72.50 g | 108.57 g | 145.0 g |

Making the Troche

A 400 mL beaker is placed on the scales and tared. The active ingredients are added. The PEG base prepared above is then added up to a total weight of 30.0 g.

The beaker is placed onto a hotplate and the stirrer bar allowed to spin. The required flavour is added, and the mixture allowed to spin until all active ingredients are dissolved.

The troche mixture is then poured into a mould and evened out with a spatula and allowed to dry.

The top of the troche is slowly heated using a hair dryer until it begins to melt.

Any excess is scraped away evenly with a clean bent spatula using the grids of the mould as a guide. The excess is used to fill any holes and even out each lozenge to an even dosage form. This may need to be repeated 2-3 times.

Once even, the surface is slightly heated to finish. The mould is then cleaned outside with a damp cloth.

Discussion

It can be seen that this methodology is not ideal for commercial scale manufacture. It would be preferable to be able to use the standard dry tabletting process for commercial scale manufacture.

Example 2

This example demonstrates the manufacture of LINGUET tablets according to the invention.

Release powders containing the equivalent of 5, 10 and 40 mg of the active ingredient sodium alendronate were blended together with the following excipients:

PEG 1000-8000 molecular weight, varied according to required hardness and time for dissolution of tablet Magnesium Stearate: 0.05-2% by weight Kollidon: 0.05-2% by weight Stevia: 0.05-2% by weight Active Ingredient: up to 60% by weight Standard dry blending was performed in a horizontal low-energy laboratory blender for 60 mins. Powder mixtures were subsequently blended with PEG for 5 mins, and directly compressed via TabletPress Inc Benchtop single press tablet punch.

Dissolution times for these LINGUET tablets range from 10 to 20 mins, while a slightly longer period of 15-20 mins was required for complete dissolution following buccal administration.

Example 3

This example investigated the bioavailability of hormone replacement therapy active ingredients using the buccal delivery system of the invention in a clinical trial in a hospital. The trial was conducted with approval of an ethics committee within the hospital.

LINGUET tablets were generated containing 17-β-oestradiol (0.5 mg), progesterone (200 mg), testosterone (2.0 mg) and DHEA (10.0 mg). The excipients in the LINGUET tablets consisted of silica gel, magnesium stearate, acacia, stevia and polyethylene glycol with a wildberry flavour. The LINGUET tablets employed in this trial were formulated in a single batch for the study using the process according to the invention as described in example 2 above. The LINGUET tablets were provided by Richard Stenlake Compounding Pharmacist (Bondi Junction, Australia).

Study Protocol

The study was an open-label investigation in six postmenopausal women. Before entry into the trial, subjects gave informed consent, and underwent medical and biochemical screening. Subjects were in general good health, and at least one year post-menopausal. The subjects ranged in age from 45 to 60 years (mean, 56 yr), had a mean weight of 69 kg (range, 64-76 kg), mean height of 166 cm (range 157-178 cm) and mean body mass index of 25.2 (range 23.4-27.6).

Subjects did not have a history of cancer of the breast or uterus, thrombosis, embolism, hypertension; diabetes, hyperlipidaemia, obesity or were smokers. They also did not have any clinically significant abnormalities on routine biochemical and haematological screening.

Subjects discontinued their prescribed HRT therapy as well as any herbal or alternative medicines not less than three days prior to the first study day. Subjects presented to the Clinical Trials Centre on the morning of each study day after an overnight fast. An indwelling cannula was inserted into a forearm vein and a baseline blood specimen collected.

On the first day, a half-LINGUET tablet was placed in the buccal cavity (between the cheek and the gum) and allowed to dissolve. Subjects were instructed not to swallow the formulation. Dissolution of the formulation in the buccal cavity took up to 40 min. Subjects rinsed their mouths with water at 45 min. Blood samples were collected via the cannula at timed intervals over 24 h. Subjects were discharged, but continued to take half a LINGUET tablet, twice daily, for the following two weeks. Subjects then re-presented to the Clinical Trials Centre where the morning dose was taken and further blood samples were collected at timed intervals over the dosage interval of 12 h.

Blood samples were schedule for collection following the single dose at the following times:
Pre-dose (0), 0.25, 0.5, 0.75, 1.0, 1.5, 2.0, 3.0, 4.0, 6.0, 8.0, 12.0, 16.0, 20M and 24.0 h following the single dose, and at pre-dose (0), 0.25. 0.5, 0.75, 1.0, 2.0, 2.5, 3.0, 4.0, 6.0, 8.0, 10.0 and 12 h after the two-week dosing interval (steady-state). Actual times were recorded, and these were used for the pharmacokinetic calculations.

Saliva was collected according to the standardized directions provided by the laboratory, Australian Reference Laboratories (Melbourne), and stored frozen (−20° C.) prior to shipping for hormonal analysis. In brief, subjects rinsed their mouths thoroughly with water and waited 5-10 min before swallowing any saliva in the mouth. Subjects then expressed saliva directly into the collection tubes.

Saliva samples were obtained for single dose estimation at the following times: pre-dose (0), and 1.0, 4.0, 8.0, 12.0, 16.0 and 24 h after dosing. For steady-state analysis, saliva was collected at pre-dose (0), and 1.0, 4.0, 8.0 and 12.0 h after LINGUET tablet administration.

Analytical Methods

Plasma concentrations of hormones were determined using routine validated, radioimmunoassay techniques in the hospital laboratory (Sydpath, St Vincent's Hospital, Sydney). The laboratory is an accredited pathology provider that participates in national quality assurance programmes for hormonal analysis.

Hormone concentrations in saliva were conducted by the Analytical Reference Laboratories (Melbourne) using validated, commercial radioimmunoassays. This laboratory is similarly an accredited pathology provider.

DHEA was monitored as the sulphate metabolite (DHEAS), not as the administered hormone.

Oestradiol:

Single and multiple dosing of the LINGUET tablet produced very similar mean concentration-time profiles for oestrogen in plasma. Substantial intersubject variability on concentrations was evident (Tables 3 and 4).

Testosterone:

Single and multiple dosing of the LINGUET tablet also produced virtually super-imposable mean concentration-time profiles for testosterone in plasma with markedly increased concentrations for up to 4 hours, and a return to pre-treatment values within approximately 8 hours. Absorption of this hormone was more rapid than for the others with peak concentrations occurring at a mean of 0.6 hr (Tables 3 and 4).

Progesterone:

Progesterone demonstrated the greatest accumulation on dosage to steady-state (Table 3). Elimination of this hormone appeared to be biphasic with a secondary peak evident at approximately 4 hr both following single and multiple dosing. Concentrations decreased to below those generally associated with biological activity in the endometrium within five hours.

Dehydroepiandrosterone (DHEA):

Single dose administration of one-half LINGUET tablet (5 mg DHEA) resulted in a doubling of blood concentrations of DHEAS over 5-10 hours with a subsequent return to pre-treatment concentrations within 24 hr. Inter-subject variability was high (Tables 3 and 4).

Results and Discussion

Concentration Profiles of Hormones in Saliva:

Before the single application of a LINGUET tablet, the salivary concentrations of all four hormones appeared to be elevated compared to blood concentrations. The concentrations of oestradiol and progesterone in saliva were elevated many times higher than in blood following use of the LINGUET tablet. This elevation was maintained over the following 8-12 hours suggesting that the massive increase was not due solely to residual hormone within the buccal cavity (Table 5—see FIG. 6).

At steady-state, the concentrations of salivary hormones were found to be elevated to unexpectedly high concentrations. Ratios of saliva top plasma was very variable (Table 5—see FIG. 6).

Plasma Hormones:

Each of the four hormones, oestradiol, progesterone, testosterone and dehydroepiandrosterone (the latter monitored as the active sulphate metabolite) were readily absorbed from the LINGUET tablet and achieved concentrations found in normal young menstruating women. Peak concentrations were achieved quite quickly, with a return to baseline between 4 and 8 hours after the single dose. The profiles at steady-state were very similar for oestrogen and testosterone reflecting their short half-lives with respect to the dosing interval. By contrast, at steady-state progesterone was sustained at concentrations usually associated with physiological and biological activity in young normal women. If this sustained concentration of progesterone is shown to produce inhibition of mitosis in the endometrium or result in develop of secretory change, then this route of delivery of progesterone could be utilised for management of post-menopausal symptoms.

The advantage of the buccal route of delivery is that it allowed rapid absorption of the hormones and physiological concentrations were achieved. This formulation avoids the first-pass metabolism associated with oral administration, while also obviating the difficulties commonly associated with transdermal application, namely erratic and poor absorption.

TABLE 3

Baseline hormone concentrations of six postmenopausal women prior to troche administration and after two weeks of twice daily administration

| Hormone | Prior to administration | Trough concentration at steady-state |
|---|---|---|
| Oestradiol (pmol/L) | 71.5 ± 114.2 | 96.0 ± 33.8 |
| Testosterone (nmol/L) | 0.38 ± 0.08 | 0.67 ± 0.28 |
| Progesterone (nmol/L) | 1.35 ± 0.73 | 6.35 ± 2.82 |
| DHEA-sulphate (nmol/L) | 1.29 ± 0.80 | 2.56 ± 1.99 |

TABLE 4

Maximum hormone concentrations (Cmax) and the time they occurred (Tmax) after the first dose (Day 1) and after two weeks of treatment (steady-state)

| | Day 1 | | Steady-state | |
|---|---|---|---|---|
| Hormone | Cmax | Tmax | Cmax | Tmax |
| Oestradiol (pmol/L) | 1685 ± 1071 | 1.1 h | 1821 ± 581 | 1.0 h |
| Testosterone (nmol/L) | 31.6 ± 10.9 | 0.6 h | 31.6 ± 5.0 | 0.6 h |
| Progesterone (nmol/L) | 22.9 ± 6.9 | 1.5 h | 26.1 ± 7.6 | 1.0 h |
| DHEA-sulphate (nmol/L) | 2.2 ± 1.1 | 6.0 h | 4.0 ± 2.0 | 1.5 h |

Table 5 shows the results of a single dose LINGUET tablet on day 1 when testing mean hormone concentrations in blood and saliva.

CONCLUSION

The LINGUET tablets which contained the buccal delivery system according to the invention delivered the hormones via the buccal cavity into the blood. The results obtained are comparable with those published for the prior art troches in Wren et al, "Pharmacokinetics of estradiol, progesterone, testosterone and dehydroepiandrosterone after transbuccal administration to postmenopausal women" *Climacteric* 2003, 6:104-111.

The word 'comprising' and forms of the word 'comprising' as used in this description and in the claims does not limit the invention claimed to exclude any variants or additions.

Modifications and improvements to the invention will be readily apparent to those skilled in the art. Such modifications and improvements are intended to be within the scope of this invention.

The invention claimed is:

1. A buccal delivery formulation comprising a matrix consisting of:
   (a) up to 60% by weight of the total matrix of one or more bisphosphonic acids or bisphosphonate salts selected from the group consisting of alendronate, etidronate, pamidronate, tiludronate, risedronate compounds, and mixtures thereof;
   (b) q.s. of one or more polyethylene glycols or PEG-fatty acid esters having surfactant properties selected from the group consisting of PEG 1450, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto 25 sterol, PEG-30 soya sterol, PEG-20 trioleate, PEG-40 sorbitan oleate, PEG-80 sorbitan laurate, PEG-1450, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, polysorbate, a poloxamer, and mixtures thereof;
   (c) 0.05-2% by weight of the total matrix of one or more suspending agents selected from the group consisting of tetragonolobus, *Acacia glaucophylla, Acacia abyssinica, Acacia nilotica, Acacia gummifera, Acacia Arabica*, silica gel, povidone, polyvinyl alcohol-polyethylene glycol graft-copolymer, polyethylene glycol (15)-hydroxystearate, (a mixture of lactose monohydrate, povidone and crosspovidone) and mixtures thereof;
   (d) 0.05-2% by weight of the total matrix of magnesium stearate; and
   (e) 0.05-2% by weight of the total matrix of one or more sweeteners selected from the group consisting of sucrose, sucralose, zinc gluconate, ethyl maltitol, glycine, acesulfame-K, aspartame, saccharin, fructose, xylitol, honey, corn syrup, golden syrup, misri, spray dried licorice root, glycerrhizine, dextrose, sodium gluconate, stevia powder, glucono delta-lactone, ethyl vanillin, vanillin, normal and high-intensity sweeteners or syrups or salts thereof and mixtures thereof.

2. The buccal delivery formulation according to claim 1 wherein the buccal delivery formulation is suitable for sublingual administration.

3. The buccal delivery formulation according to claim 1 wherein the buccal delivery formulation is suitable for sustained release administration.

4. The buccal delivery formulation according to claim 1 wherein the polyethylene glycol (PEG) is PEG 1450.

5. The buccal delivery formulation according to claim 1 wherein the sweetener is a high-intensity sweetener selected from the group consisting of aspartame, sucralose, and acesulfame-K.

6. The buccal delivery formulation according to claim 1 wherein the bisphosphonate is an alendronate selected from the group consisting of anhydrous alendronate, hydrated alendronate salts and mixtures thereof.

7. The buccal delivery formulation according to claim 6 wherein the alendronate is sodium alendronate.

8. A method of manufacturing a buccal delivery formulation according to claim 1 consisting of the steps of:
   (a) preparing a matrix by blending
      (i) up to 60% by weight of the total matrix of one or more bisphosphonic acids or bisphosphonate salts selected from the group consisting of alendronate, etidronate, pamidronate, tiludronate and risedronate compounds and mixtures thereof;
      (ii) q.s of one or more polyethylene glycols or PEG-fatty acid esters having surfactant properties selected from the group consisting of PEG 1450, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto 25 sterol, PEG-30 soya sterol, PEG-20 trioleate, PEG-40 sorbitan oleate, PEG-80 sorbitan laurate, PEG-1450, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, polysorbate, a poloxamer, and mixtures thereof;
      (iii) 0.05-2% by weight of the total matrix of one or more suspending agents selected from the group consisting of tetragonolobus, *Acacia glaucophylla, Acacia abyssinica, Acacia nilotica, Acacia gummifera, Acacia Arabica*, silica gel, povidone, polyvinyl alcohol-polyethylene glycol graft-copolymer, polyethylene glycol (15)-hydroxystearate, (a mixture of lactose monohydrate, povidone and crosspovidone) and mixtures thereof;
      (iv) 0.05-2% by weight of the total matrix of magnesium stearate; and
      (v) 0.05-2% by weight of the total matrix of one or more sweeteners selected from the group consisting of sucrose, sucralose; zinc gluconate; ethyl maltitol; glycine; acesulfame-K; aspartame; saccharin; fructose; xylitol; honey; corn syrup, golden syrup, misri, spray dried licorice root; glycerrhizine; dextrose; sodium gluconate; stevia powder; glucono delta-lactone; ethyl vanillin; vanillin; normal and high-intensity sweeteners or syrups or salts thereof and mixtures thereof; and
   (b) compressing the matrix into a tablet format for administration to one or more membranes in the buccal cavity, wherein the ratio of component (i) to components (ii)-(v) enables dissolution and absorption of component (i) within a desired time period.

* * * * *